United States Patent
Divekar et al.

(10) Patent No.: US 10,040,774 B2
(45) Date of Patent: Aug. 7, 2018

(54) PREPARATION OF FURFURAL USING MIXED SOLVENTS

(71) Applicant: BASF SE, Ludwigshafen am Rhein (DE)

(72) Inventors: Sunil Sadashiv Divekar, Pune (IN); Pramod Shankar Kumbhar, Pune (IN); Rahul Vasantrao Bagal, Pune (IN); Amit Madanlal Katariya, Pune (IN)

(73) Assignee: BASF SE, Ludwigshafen am Rhein (DE)

(*) Notice: Subject to any disclaimer, the term of this patent is extended or adjusted under 35 U.S.C. 154(b) by 0 days.

(21) Appl. No.: 15/543,676

(22) PCT Filed: Jan. 13, 2016

(86) PCT No.: PCT/IB2016/050138
§ 371 (c)(1),
(2) Date: Jul. 14, 2017

(87) PCT Pub. No.: WO2016/113678
PCT Pub. Date: Jul. 21, 2016

(65) Prior Publication Data
US 2018/0002304 A1  Jan. 4, 2018

Related U.S. Application Data

(63) Continuation of application No. PCT/IN2015/000127, filed on Mar. 16, 2015.

(30) Foreign Application Priority Data

Jan. 14, 2015 (IN) .............. 139/MUM2015

(51) Int. Cl.
*C07D 307/50* (2006.01)

(52) U.S. Cl.
CPC .................. *C07D 307/50* (2013.01)

(58) Field of Classification Search
CPC ................................... C07D 307/50
USPC ........................................ 549/489
See application file for complete search history.

(56) References Cited

U.S. PATENT DOCUMENTS

| | | | |
|---|---|---|---|
| 4,533,743 A | 8/1985 | Medeiros et al. | |
| 2012/0302767 A1 | 11/2012 | Dumesic et al. | |
| 2013/0204039 A1 | 8/2013 | Runge | |

FOREIGN PATENT DOCUMENTS

| | | |
|---|---|---|
| WO | 2012162001 A1 | 11/2012 |
| WO | 2013102911 A1 | 7/2013 |
| WO | 2014009521 A1 | 1/2014 |
| WO | 2015020845 A1 | 2/2015 |

(Continued)

OTHER PUBLICATIONS

ISR/Written Opinion for PCT/IB2016/050138 dated Apr. 28, 2016.
(Continued)

*Primary Examiner* — Taylor V Oh
(74) *Attorney, Agent, or Firm* — Armstrong Teasdale LLP

(57) ABSTRACT

Processes for the preparation of furfural from a xylose containing feedstock and more particularly to an elevated temperature conversion of a xylose containing feedstock to furfural in acidic conditions are described. The described process uses a mixture of two solvents in which the humins are formed and solubilized. The described process is operated in continuous mode with no significant amounts of solid by-products formation.

20 Claims, 1 Drawing Sheet

(56) References Cited

FOREIGN PATENT DOCUMENTS

| WO | 2015034964 A1 | 3/2015 |
|----|---------------|--------|
| WO | 2015/066598 A1 | 5/2015 |

OTHER PUBLICATIONS

ISR/Written Opinion for PCT/IN2015/000127 dated Dec. 8, 2015.
International Preliminary Report on Patentability for PCT Patent Application No. PCT/IB2016/050138, dated Jul. 27, 2017, 9 pages.

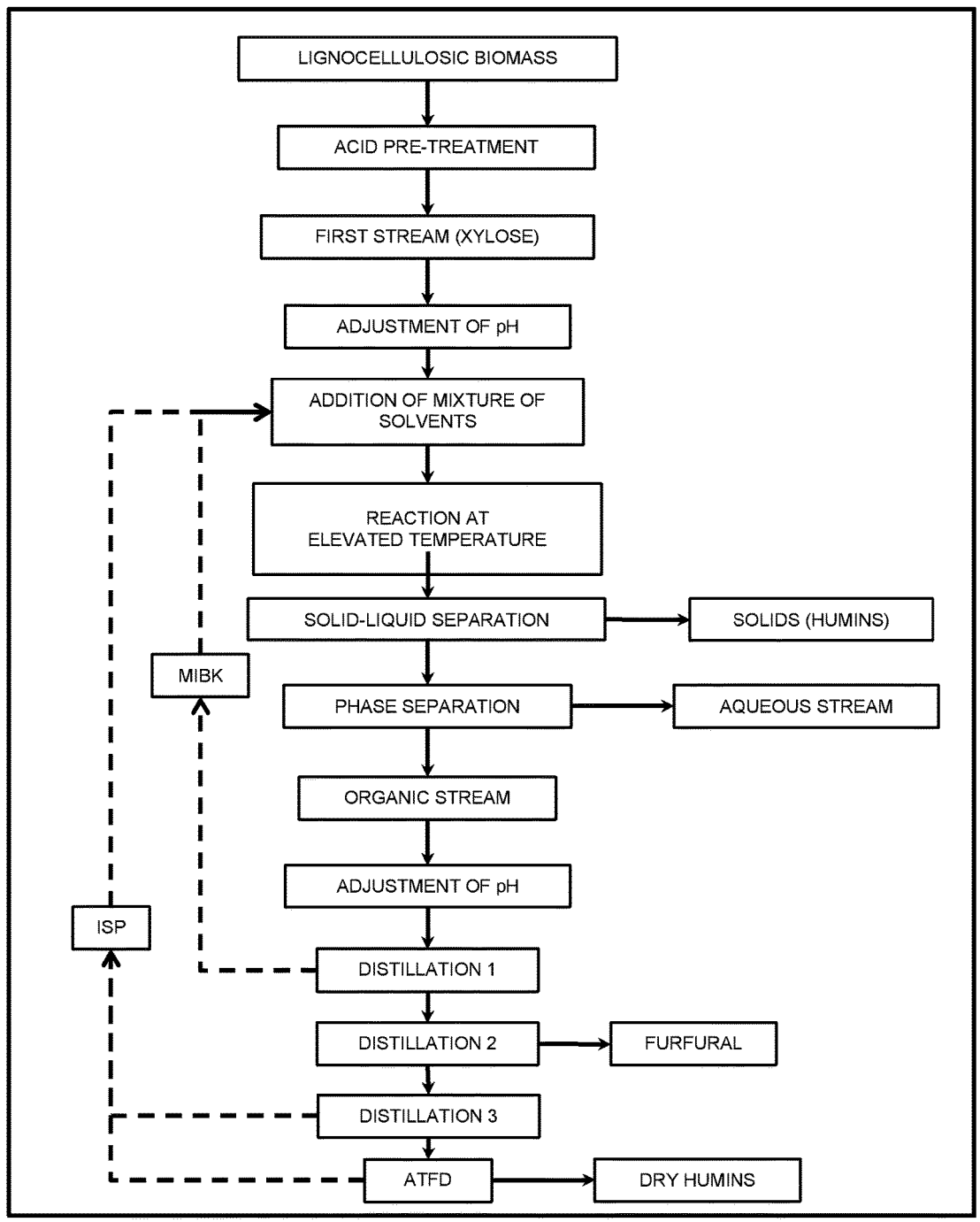

PREPARATION OF FURFURAL USING MIXED SOLVENTS

CROSS-REFERENCE TO RELATED APPLICATIONS

This application is a U.S. National Phase Application of PCT Application No. PCT/IB2016/050138, filed Jan. 13, 2016, which claims the benefit of priority to Indian Patent Application No. 139/MUM/2015, filed Jan. 14, 2015. PCT Application No. PCT/IB2016/050138 is a continuation of PCT Application No. PCT/IN2015/000127, filed Mar. 16, 2015, which also claims the benefit of priority to Indian Patent Application No. 139/MUM/2015, filed Jan. 14, 2015, the entire contents of which are hereby incorporated by reference herein.

BACKGROUND OF THE INVENTION

Any of the documents cited herein are incorporated by reference in their entirety.

A process for the production of Furfural from pentoses using a continuous plug flow reactor is described in U.S. Pat. No. 4,533,743. This patent is also cited in the application WO 2015/020845 A1. This international application is directed to a process for producing furan from furfural from biomass.

A further process for producing furfural from hemocellulose sugars is disclosed in WO 2015/034964 A.

The invention relates to an improved process for the preparation of furfural from a xylose containing feedstock and more particularly to an elevated temperature conversion of a xylose containing feedstock to furfural in acidic conditions. The said process using isophorone or a mixture of two solvents in which condition humins formed are solubilised in the solvents and process is operated in continuous mode with no significant amounts of solid by-products formation.

Furfural is an important renewable and non-petroleum based platform chemical feedstock. It is aldehyde of pyromucic acid with properties similar to those of benzaldehyde. It is widely used as a solvent for refining lubricating oils in petrochemical industry. Furfural is further used as a chemical intermediate in the production of the solvents like furan and tetrahydrofuran. Tetrahydrofuran is further converted to the starting materials used for the preparation of NYLON. Furfural has also been used as fungicidal and weedicidal agents. Furan derivatives such as hydroxymethylfurfural (HMF), furfural and furfuryl alcohol are derived from renewable biomass resources; and serve as building blocks for other potential transportation fuels including dimethylfuran and ethyl levulinate. These derivatives can be used either by themselves or with phenol, acetone or urea to make solid resins. Such resins are used in making fibreglass, aircraft components, automotive brakes, etc.

Conventionally furfural is produced by the dehydration of pentose sugars obtained from cornstalks and corncobs, husks of oat and peanut and other waste biomass stocks [lignocellulosic materials—LCM]. The pentose [C5] fraction of biomass is primarily utilized in bio-refineries to produce furfural, a useful platform chemical produced from the biomass. One of the conventional methods of producing furfural is by acid dehydration of pentosans contained in said biomass. The conventional batch-furfural production process is characterised by high losses of furfural due to the formation of resinous substances called humins, which gives a yield of less than 50%. This process also needs a lot of steam and generates plenty of effluent waste. This method further has a disadvantage of high cost. By another conventional method, furfural is produced by a catalytic process of converting biomass into furfural. This process is a biphasic process, which gives better yield, but the reaction system is homogeneous, corrosive and maximum 10% xylose can be used at the small-scale reactions. Therefore, there is need for more effective and efficient methods of furfural preparation from a variety of biomass feed stocks. With the prior art's methods it has been very difficult to process xylose containing feed streams from LCM with xylose contents of 10% or more, let alone 20% or more.

Further, the humins formed are insoluble in the solvents conventionally used in the preparation of furfural from xylose from LCM biomass. This leads to processes wherein in continuous production process cannot be developed due to accumulation of insoluble humins and heat transfer issues in the system, and therefore, batch processing is performed routinely. The batch processes are expensive and capital intensive compared with continuous processes in bulk chemical industry. Hence, there is need to developing a continuous process for the production of furfural from LCM containing xylose biomass for economic as well as technological benefits.

OBJECTS OF THE INVENTION

It was an object of the instant invention to provide an efficient process, particularly a continuous process, for the production of furfural from a variety of biomass feedstocks, particularly lignocellulosic materials containing xylose biomass, which is improved in comparison with the previous processes of the prior art, especially in that the reaction apparatuses become less clogged with side products as humins, e.g. avoiding sticky, insoluble humins.

It was a further object to provide a favourable process, also from an economical point of view, especially in an industrial scale.

SUMMARY OF THE INVENTION

The object of the instant invention has been solved by the matter outlined in present claim 1. The dependant claims as well as the description and examples show further embodiments of the present invention.

DEFINITION OF TERMS

The following description is made for the purpose of illustrating the general principles of the present invention and is not meant to limit the inventive concepts claimed herein. Further, particular features described herein can be used in combination with other described features in each of the various possible combinations and permutations.

Unless otherwise specifically defined herein, all terms are to be given their broadest possible interpretation including meanings implied from the specification as well as meanings understood by those skilled in the art and/or as defined in dictionaries, treatises, etc.

It must also be noted that, as used in the specification and the appended claims, the singular forms "a", "an" and "the" include plural referents unless otherwise specified.

As used herein, the term "about" when combined with a value refers to plus and minus 10% of the reference value unless otherwise specified. For example, a temperature of about 50° C. refers to a temperature of 50° C.±5° C., etc.

Any indications of quantity given in the instant invention are to be considered as indications of quantity by weight, if not specified otherwise.

In the instant invention are the given reactions or process steps are carried out at normal pressure/atmospheric pressure, that is at 1013 mbar. Additionally, any reference to "bar" or "bars" is to be understood as $bar_{absolute}$, if not specified otherwise.

In the instant invention the term "and/or" includes any and all combinations of one or more of the associated listed items.

An industrial scale process according to the present invention means a large scale process or medium scale process, in other words as educts amounts of at least one kg preferably at least 3 kg are used.

DETAILED DESCRIPTION

Lignocellulosic biomass [LCM] constitutes the majority of agricultural waste organic matter such as straw, cornhusk, wheat, sugarcane bagasse, corn stover, wood chips, saw dust as well as organic fraction of municipal solid waste. It has three major components cellulose, hemicellulose and lignin. The carbohydrate polymers such as cellulose and hemicellulose contain different sugar monomers whereas lignin is a complex aromatic polymer synthesized from phenylpropanoid precursors. Hemicellulose is a low molecular weight heteropolysaccharide chain containing two different sugar monomers such as hexoses (glucose, mannose and galactose) and pentoses (arabinose and xylose). The hemicellulose present in biomass, preferably LCM, undergoes hydrolysis in acidic media to form xylose. The lignocellulosic feedstock is the sole source to get xylose in nature.

In one embodiment of the present invention disclosed herein a process for the efficient conversion of xylose, preferably obtained from biomass, preferably LCM, to furfural comprising seven steps namely:
1] Acid Pretreatment;
2] pH Adjustment;
3] Solvent (Mixture) Addition;
4] Product Preparation;
5] Phase Separation;
6] pH Adjustment of Organic Phase;
7a] Optionally Separating Low Boiling Solvent;
7] Recovery of Furfural; and
8] Recycle and/or Recovery of High Boiling Solvent.

Each step may comprise one or more elements for performing specific or optional functions as required for achieving conversion of xylose to furfural. A person skilled in the art may appreciate different variations and/or combinations of these elements that may be used to perform the objects of the invention disclosed herein.

In another embodiment no tetralin at all is used during the process of the invention, especially no tetralin is present in any of the streams respectively solutions present in the process according to the invention.

Step 1: Acid Pretreatment

Lignocellulosic biomass [LCM], preferably selected from the group consisting of corn cob, corn stover, bagasse or mixtures thereof, as feedstock is pre-treated with mineral or organic acids, preferably selected from the group consisting of $H_2SO_4$, $H_3PO_4$, oxalic acid and mixtures thereof, and insoluble fraction is removed; the soluble fraction comprising xylose and the acids forms a first stream. In one embodiment a combination of $H_2SO_4$ about 1.5% by weight and oxalic acid about 0.5% by weight is used for the acid pretreatment. This first stream is adjusted to comprise between 5 to 30% by weight of xylose, preferably 10 to 25% by weight, more preferably 10 to 24, 23, 22 or 21%, especially 10 to 20% by weight and generally comprises at least 10% by weight of xylose and comprises about 2% by weight of said acids. In one embodiment the xylose content is between 10 to 30% xylose.

In one alternative, in this first step a stream, e. g. a fluid comprising or consisting of the soluble fraction of the acid treatment of LCM comprising xylose and the acids is discharged into a reactor respectively reactor vessel.

In one embodiment no additional salt (or salts) or aqueous solution thereof are added during the process according to the invention. In one alternative no additional salt (or salts) or aqueous solution thereof are added in step 1 of the process according to the invention. The streams respectively the solutions of the invention, especially in step 1, may comprise salt, especially sulphate and/or phosphate salts, which are formed due to chemical reaction in situ, but no active addition of salt(s) takes place.

A salt is defined, according to the present invention, as a compound resulting from a chemical reaction between an acid and a base, in which the acid's hydrogen atoms are replaced by cations of the base. Cations are metal cations or quaternary ammonium cations.

In one embodiment the C5 stream is used as such after LCM pre-treatment, without any further treatment or purification.

In one embodiment of the present invention, said reactor vessel is an autoclave vessel. In another embodiment of the present invention, said reactor is a batch type closed stirred tank reactor. In yet another embodiment of the present invention, said reactor is a plug-flow reactor. In yet another, preferred embodiment of the present invention, said reactor is a continuous stirred-tank reactor or a continuous plug-flow reactor.

In alternatives, the reactor used may be stirred-tank type, mechanically agitated stirred type or continuous type.

In another alternative the first stream is treated according to step 2 in an arbitrary, suitable vessel.

Step 2: pH Adjustment

The pH of said first stream is adjusted using a base, preferably a metal oxide or hydroxide, more preferably an alkali or earth alkali oxide or hydroxide, even more preferably NaOH or MgO, to a pH between about 1 and about 2, preferably between about 1.4 and about 1.8, most preferably about 1.6, forming a second stream.

In one alternative the second steam is discharged in a reactor as defined above. In another alternative the second stream is mixed with solvent(s) in an arbitrary, suitable vessel.

Step 3: Solvent Addition

The second stream is mixed with isophorone, or a mixture of solvents, preferably a mixture of one solvent that has a boiling point above that of furfural (high boiling solvent), preferably isophorone, with one solvent that has a boiling point below that of furfural (low boiling solvent), most preferably methyl isobutyl ketone [MIBK] with isophorone [ISP] or toluene with ISP, forming a third stream. When two solvents are used, one solvent has lower boiling point than the final product [furfural] and the second solvent has higher boiling point than said final product.

As low boiling solvents those selected from the group consisting of MIBK, toluene and mixtures thereof are preferably used in the context of the present invention.

As high boiling solvents those selected from the group consisting of isophorone, diphenyloxide [DPO], sec-butylphenols [SBP] and mixtures thereof are preferably used in the context of the present invention; especially preferred is isophorone.

Any combination of more than two solvents according to the above disclosed teaching is possible.

The ratio of aqueous phase to organic phase in this step is adjusted to be from 1:0.5 to 1:3.5, preferably 1:0.75 to 1:3.2 by weight.

In one embodiment the pH is adjusted to between about 1 to about 2.2.

Step 4: Product Preparation

In this step said third stream is subjected to a high temperature of between about 160° C. to about 220° C., preferably between about 170° C. to about 210° C., more preferably between about 180° C. to about 200° C., for between about 10 minutes to about 2 hours in a high pressure and high temperature reactor as defined above leading to the formation of a fourth stream. The residence time of the reaction mass is between about 10 minutes to about 2 hours at a high temperature of between about 160° C. to about 220° C., preferably between about 170° C. to about 210° C., more preferably between about 180° C. to about 200° C. At these conditions xylose present in the reaction mixture [said third stream] is converted to furfural due to acidic dehydration.

The conversion of xylose to furfural is performed in a reactor vessel as disclosed under step 1. The reaction mixture is subjected to an elevated temperature and pressure (the pressure resulting from the temperature and the boiling point of the solvent(s)) for a desired time-period in the presence of homogenous acid catalysts remaining from the acid pretreatment leading to the efficient production of the product.

It has surprisingly been found in the context of the present invention that the use of isophorone as solvent has the effect that the majority of the humins remain solved and do not clog the reaction apparatus. It was further surprising that this effect remains when isophorone is mixed with another, low boiling solvent, meaning that the mixture of isophorone with low boiling solvent, in particular MIBK and/or toluene, can be used to lower the costs. In one embodiment a mixture of at least two solvents comprising or consisting of a high boiling solvent, preferably isophorone, with one solvent that has a boiling point below that of furfural (low boiling solvent) is used.

This effect means that the humins are not sticky and rinse of the apparatuses with the solvent (mixture) or can after removal of the solvent easily be rinsed with water. Additionally, the humins are different in their structure than those remaining from conventional processes, because even when they are dried, they are very porous or even pulverulent and nearly free flowing and can be easily removed from the surfaces, whereas the humin-remains according to the prior art are very persistent and need considerable mechanical force or severe chemical conditions (like caustic washing or nitric acid) to be removed from the surfaces they adhere to.

Solubility and stickiness of the humins depend on the conditions of the process.

Additionally, it was a surprising finding of the present invention that the humins that are dissolved in the solvent (mixture) do not adversely affect the reaction procedure. To that effect the humin containing solvent fraction can even be recycled and re-used several times until the humin content becomes impracticably high.

This means that the deposits on the apparatuses have less layer thickness, are more easily cleaned off for instance with water rinsing or a simple cloth and the number of cycles the apparatuses can run before they have to be cleaned is considerably higher.

Step 5: Phase Separation

After completion of reaction in step 4, on conversion of more than 90% of xylose, the reaction mass [said fourth stream] is cooled to room temperature and a solid fraction can in one embodiment of the invention be separated from liquid fraction using a solid-liquid separator, for example by filtration or using a decanter or decanter centrifuge. This leads to the removal of waste and insoluble humins, if present, from said reaction mass.

Liquid fraction of the reaction mass is subjected to phase separation into an aqueous stream phase and an organic stream phase respectively.

In one embodiment of the invention the concentration of furfural in this step is at least 2%, at least more than 2%, preferably between 2 and 10%, more preferably between 3 and 9%, especially 5 to 8%.

Step 6: pH Adjustment of Organic Stream

The pH of said organic stream is adjusted to between 6 and 7 with a base like NaOH, monoethanolamine or sodium bicarbonate, preferably the base is selected from one or more of these three.

Step 7a: Optional Distillation Separating Low Boiling Solvent

In the alternative where a mixture of solvents, preferably a mixture of one solvent that has a boiling point above that of furfural (high boiling solvent), preferably isophorone, with one solvent that has a boiling point below that of furfural (low boiling solvent) is used, the low boiling solvent is separated and recovered/recycled for step 3.

The remaining fraction comprising or consisting of furfural, the high boiling solvent, preferably ISP, and the humins solved therein are processed according to step 7.

In one embodiment, a mixture of low boiling solvent, preferably MIBK or toluene, more preferably MIBK with ISP allows a very efficient and economical process. In the distillation step furfural and the low boiling solvent are distilled in a stable form. This distillation step preferably is a vacuum distillation. Furfural and the low boiling solvent can be easily separated in a further distillation.

The low boiling solvent(s) is recycled for step 3 and may be used any number of times in the process without any significant loss of mass and the distillation and recovery systems are effective and the solvent is purified to about 99% of its mass.

Step 7: Separation of Product: Furfural

The organic stream is subjected to a first distillation. In the alternative wherein only ISP is used as solvent, the organic stream of step 6 is subjected to distillation at a higher temperature, e.g. more than 162° C. (the boiling point of furfural) and less than 215° C. (the boiling point of ISP) and, preferably, under vacuum to obtain commercially pure furfural as a final product and a residual organic stream. The same proceeding is applied to the remaining fraction of step 7a.

These steps afford more than 90% conversion of xylose into furfural with final product yield of at least 60% of furfural from total xylose present in the feedstock. Further the purity of furfural at this step is about 98% of its mass.

If desired the furfural can be further purified.

The remaining fraction comprises ISP and the solved humins.

Step 8: Recycle & Recovery of High Boiling Solvent

The residual organic stream of step 7 comprises said high boiling solvent with dissolved humins. This stream can then be (re-)used in the process as such several times, particularly for up to 5 times without any treatment but the addition of low-boiling solvent for keeping the ratio of low boiling solvent to high boiling solvent, e.g. MIBK:ISP or toluene:ISP, constant to create said mixture of solvents described in step 3.

In one embodiment the humins are dissolved in the high boiling solvent, preferably isophorone. From this mixture 80% of ISP can be recovered, preferably by distillation. In an additional separation, preferably in thin-film evaporation the humins are separated from the remaining ISP.

By this way 99% of Isophorone can be recovered as well as 99% from the other solvents.

In another embodiment, after about 5 recycles as the humins faction increases up to 60% of total mass, then said residual organic stream is usually replaced or, preferably is subjected to separation as described above to obtain the high boiling solvent in pure form free of any dissolved impurities of humins or other compounds, which is again used in said process.

The removed impurities can be used otherwise or be disposed of.

The process of invention disclosed herein has, apart from those already mentioned, several advantages over the known methods of the prior art:

1] The present process is less corrosive to the equipment;

2] The process is less capital intensive with lower utility costs;

3] The process works for a stream containing higher concentration of xylose [even about 20% by weight or more] at a large scale, preferably for a stream containing xylose in a concentration of 30%, more preferably 25%, 24%, 23%, 22% or 21% especially 15 to 20%;

4] The process results into more than 90% conversion of xylose and yielding more than 60% of furfural; and 5] In this process the major part of humins is soluble in the high-boiling solvent, most preferably isophorone, [at the reaction temperature] giving advantage that the system is not clogged by insoluble humins as happens in conventional methods.

Additionally isophorone is an expensive solvent. Therefore a process for the production of furfural using as solvent isophorone might be unfavourable from an economical point of view.

The yield differences regarding a combination of isophorone with at least a second solvent are minor.

Isophorone has the following advantages: The formed humins are soluble in isophorone. Therefore clogging of the reactor is prevented and in turn no cleaning is required. The reactor can be used for several cycles. Additionally, as the humins remain soluble in isophorone it becomes easier to remove furfural upfront without degradation by distillation. The humins are separated in a second step. By this way at least 90%, preferably 91%, 92%, 93%, 94%, 95%, 96%, 97%, especially at least 98% and 99% of the isophorone is recycled.

Using only MIBK has also some disadvantages: As the boiling point of MIBK is lower than the boiling point of furfural the humins remain in the furfural fraction wherein they are solved. A further separation of Furfural and humins is very difficult.

The combination of a high boiling solvent, preferably isophorone with at least a second, low boiling solvent has significant economical advantages. When using only isophorone as a solvent, the whole quantity of isophorone has to be recovered from the humins.

Using a mixture of isophorone with at least a second solvent, especially a mixture wherein the ratio of the second solvent to isophorone is at least 1:1, 2:1, preferably 3:1 and especially 4:1 or more the quantity of isophorone recovered from humins is merely a fraction.

In conclusion, cost can be saved by using a second solvent cheaper than isophorone additionally by saving energy for the recovery of the solvents.

This provides for development of a continuous production process as all components are in liquid form and can be easily removed from different units of the production system.

In another embodiment of the present invention a process for producing furfural from xylose using less corrosive acids like oxalic acid, $H_3PO_4$ and $H_2SO_4$ in pre-treatment of LCM [lignocellulosic materials] is provided that leads to less damage to capital equipment and is eco-friendly.

In one embodiment no HCl is used as acid.

In an other embodiment the product preparation (according to step 4) is performed at an autogenous pressure of 10 to 20 bar, preferably 12 to 18 bar, especially (about) 15 bar and/or without the use of protective or inert gas, like nitrogen or argon.

In one embodiment of the present invention, a process for converting xylose to furfural comprises taking a xylose-containing stream obtained from acid pre-treated LCM. Then the pH of this stream is adjusted to between about 1 to about 2 using a metal oxide or hydroxide like sodium hydroxide or magnesium oxide. Then to this aqueous part is added about 0.5 to about 3.5, preferably about 1 to about 3 times its weight a mixture of solvents like toluene, MIBK, SBP or DPO with isophorone, as a high boiling solvent that dissolves humins formed in the reaction, to create a reaction mass. Then further subjecting said reaction mass to a temperature of about 160 to about 220° C., preferably about 180° C., for about 1 hour. On the completion of reaction, optionally an insoluble fraction is removed followed by separation of organic and aqueous parts. In the next steps, furfural and solvent are distilled out from said organic part separately. Furfural so formed is further subjected to purification or polishing steps to obtain chemically pure furfural, while the solvents are reused for the next cycle of preparation of furfural from a xylose containing feedstock.

In one embodiment of the present invention, the contact between the reaction mass [said third stream] and the acid catalysts is maintained at a temperature in the range from about 160° C. and 220° C. In another embodiment of the present invention, the contact between the reaction mass [said third stream] and the acid catalysts is maintained for a time-period ranging from about 10 minutes to about 120 minutes.

In another embodiment of the present invention, xylose content is analysed by liquid chromatography with a refractive index detector. BioRad Aminex 87 H+ column of size 300 mm×7.8 mm is used with 0.005 M $H_2SO_4$ as mobile phase with flow rate of 0.6 mL/min. Column oven temperature is kept at 55° C. and injection volume at 20 µL. Deionised water is used as a diluent for the sample preparation. Retention time of xylose is observed at 9.47 minute. Estimation of xylose in the test samples is done using calibration graph generated using five known concentration of a xylose standard.

In yet another embodiment of the present invention, furfural content is analysed by gas chromatography with a flame ionisation detector. ALLTECH AT-Wax column of 60 meters length is used with ID of 0.53 micron. Nitrogen is used a mobile phase. Dimethylformamide (DMF) is used as the dilution medium and other conditions of operation are kept standard as per manufacturer's manual.

Representative features of an embodiment of the invention are illustrated in the drawing. FIG. 1 depicts a process flow for the conversion of a feed stock comprising xylose to furfural in accordance with one aspect of the present invention. In the first act, said feedstock is mixed with one or more of homogenous acid catalysts. Then it is subjected to an elevated temperature and pressure leading to the formation of a pre-treated biomass from which C5 [xylose comprising] stream [first stream] is separated by filtration. This stream is further subjected to the pH adjustment and solvent addition, followed by the reaction at an elevated temperature and pressure leading to the formation of a product stream, which is separated into an organic phase stream and an aqueous phase stream. However, humins formed can in one embodiment of the present invention be removed as solids from said product stream before phase separation. Said organic phase stream is then subjected to different methods of distillation depending upon the nature of the solvent used to recover furfural and solvents in pure forms.

The various embodiments of the instant invention, including those of the dependent claims, can be combined with each other in any desired manner.

DESCRIPTION OF THE DRAWING

FIG. 1 depicts a process flow diagram of a preferred embodiment of the production of furfural from a LCM feedstock comprising xylose. Different elements of the process are identified and directional movement of different streams and components formed during the process are shown to describe the features of one preferred embodiment of the present invention. The ATFD-step (agitated thin film dryer) can optionally be performed.

The invention will now be explained by way of the following non-limiting examples.

EXAMPLES

Examples provided below give wider utility of the invention without any limitations as to the variations that may be appreciated by the person skilled in the art. A non-limiting summary of various experimental results is given in the examples and tables, which demonstrate the advantageous and novel aspects of the process of using a xylose-containing stream obtained from any LCM to prepare furfural in very efficient ways as disclosed herein.

Example 1

A batch of about 118 kg of corncobs having total dry solids of about 92% by weight, cellulose of about 33% by weight, hemicelluloses of about 27% by weight and lignin of about 13% by weight was used as a feedstock. It was subjected to mechanical milling for size reduction to less than 40 mm particles affording about 108 kg of the particulate material. This particulate material was soaked in water for about 30 min. Then about 360 kg slurry containing about 30% by weight total insoluble solids was prepared and continuously introduced into a hydrolyser through a plug screw reactor. Here the slurry was mixed with about 240 liters of the admixture of oxalic and sulphuric acids. This admixture of mixed acids contained about 1.08 kg of oxalic acid and about 2.16 kg of sulphuric acid on dry biomass weight basis [total 3% acid on dry biomass weight basis]. The resultant reaction mixture was then subjected to hydrolysis in said hydrolyser at a temperature of about 160° C. and pressure of about 6 bar[absolute] for a period of about 24 minutes at pH of about 1.3. At the end of this pretreatment the final slurry of about 603 kg contained about 16% of total solids. After filtration the liquid stream (said C5 stream) contained about 0.52% of glucose, about 4.8% of xylose, about 0.05% of furfural, about 0.04% of HMF and about 3800 PPM of phenolic components along with residual cellulose and lignin as detected by the HPLC methods. Herein, the efficiency of xylan to xylose [C5] conversion was about 86% and that of glucan to glucose conversion was about 8%. Then this final liquid stream [said C5 stream] was further subjected to evaporation to concentrate the amount of xylose in said stream up to about 20% by weight and formed the concentrated feedstock stream [first stream] for the preparation of furfural according to the examples below.

Example 2 [See Table Serial No 1]

3.5 kg of a concentrated feedstock stream [first stream] comprising 10% xylose by weight was obtained from an acid pre-treated sugarcane bagasse. This stream also comprised 1-2% acid by weight used for said pre-treatment reaction. Then said first stream was subjected to pH adjustment to a pH value of 1.6 using a 50% NaOH solution forming a second stream. Then a mixture of 3500 g of methyl isobutyl ketone (MIBK) was added to second stream forming a third stream. This third stream was subjected to temperature of 180° C. in a closed stirred tank reactor working at 650 RPM for 1 hour. After completion of the heat treatment, the reaction mass was cooled to room temperature, and solids [humins] remaining in the mass removed by filtration. The humins were partially soluble [HS2] in the reaction mass and nominally sticky [S1] to the equipment. Then organic phase was separated from aqueous phase and subjected to pH adjustment to 7 by NaHCO$_3$. Further said organic phase was subjected to distillation to recover MIBK that was recycled. This method achieved 99% conversion of xylose present in the feedstock with 79% yield of furfural.

Example 3 [See Table Serial No 12]

3.5 kg of a concentrated feedstock stream [first stream] comprising 20% xylose by weight was obtained from an acid pre-treated corncob. This stream also comprised 1-2% acid by weight used for said pre-treatment reaction. Then said first stream was subjected to pH adjustment to a pH value of 1.5 using a 50% NaOH solution or magnesium oxide [MgO] forming a second stream. Then a mixture of 2800 g of methyl isobutyl ketone (MIBK) and 700 g of isophorone (80:20) was added to said second stream forming a third stream. This third stream was subjected to temperature of 180° C. in a stirred-tank reactor with at retention time of 1 hour. On completion of the heat treatment, the reaction mass was cooled to room temperature and collected. The humins were partially soluble [HS2] in the reaction mass and nominally sticky [S1] to the equipment. Then the organic phase was separated from aqueous phase and subjected to pH adjustment to about 6 to 7 by NaHCO$_3$. Further said organic phase was subjected to first distillation to recover MIBK that was recycled. The remaining organic phase contained furfural and isophorone with dissolved humins; it was subjected to a second distillation to recover furfural in pure form. This method achieved 100% conversion of xylose present in the feedstock with 78% yield of furfural. The residual organic phase mostly of isophorone and dissolved humins was recycled as such in the process for up to five times without any significant loss of yield of furfural. At the end of the fifth cycle, the residual isophorone with humins up to 60% was subjected to distillation to recover pure isophorone.

Example 4 [See Table Serial No 17]

3.5 kg of a concentrated feedstock stream [first stream] comprising 10% xylose by weight was obtained from an acid pre-treated sugarcane bagasse. This stream also comprised 1-2% acid by weight used for said pre-treatment reaction. Then said first stream was subjected to pH adjustment to a pH value of 1.5 using a 50% NaOH solution or magnesium oxide [MgO] forming a second stream. Then a mixture of 2800 g of toluene and 700 g of isophorone (80:20) was added to said second stream forming a third stream. This third stream was subjected to temperature of 180° C. in a reactor for a retention time of 1 hour. After completion of the heat treatment; the reaction mass was cooled to room temperature and collected. The humins were sparingly soluble [HS1] in the reaction mass and significantly sticky [S3] to the equipment. Then the organic phase was separated from aqueous phase and subjected to pH adjustment to about 6 to 7 by NaHCO$_3$. Further said organic phase was subjected to first distillation to recover toluene that was recycled. The remaining organic phase contained furfural and isophorone with dissolved humins; it was subjected to a second distillation to recover furfural in pure form. This method achieved 98% conversion of xylose present in the feedstock with 84% yield of furfural. The residual organic phase mostly of isophorone and dissolved humins was recycled as such in the process for up to five times without any significant loss of yield of furfural. At the end of the fifth cycle, the residual isophorone with humins up to 50% was subjected to distillation to recover pure isophorone.

Example 5 [See Table Serial No 16]

3.5 kg of a concentrated feedstock stream [first stream] comprising 20% xylose by weight was obtained from an acid pre-treated sugarcane bagasse. This stream also comprised 1-2% acid by weight used for said pre-treatment reaction. Then said first stream was subjected to pH adjustment to a pH value of 1.5 using a 50% NaOH solution forming a second stream. Then 3500 g of toluene was added to said second stream forming a third stream. This third stream was subjected to temperature of 180° C. in a closed stirred tank reactor working at 650 RPM for 1 hour. On completion of the heat treatment, the reaction mass was cooled to room temperature and collected. The humins were insoluble [HS0] in the reaction mass and significantly sticky [S3] to the equipment. Then the organic phase was separated from aqueous phase and subjected to pH adjustment to about 7 by NaHCO$_3$. Further said organic phase was subjected to first distillation to recover toluene that was recycled. The remaining organic phase contained furfural, which was distilled out next leaving undissolved humins behind. This method achieved 99% conversion of xylose present in the feedstock with 81% yield of furfural.

Example 6 [See Table Serial No 7]

3.5 kg of a concentrated feedstock stream [first stream] comprising 20% xylose by weight was obtained from an acid pre-treated sugarcane bagasse. This stream also comprised 1-2% acid by weight used for said pre-treatment reaction. Then said first stream was subjected to pH adjustment to a pH value of 1.5 using a 50% NaOH solution forming a second stream. Then 3500 g of isophorone was added said to second stream forming a third stream. This third stream was subjected to temperature of 180° C. in a closed stirred tank reactor working at 650 RPM for 1 hour. On completion of the heat treatment, the reaction mass was cooled to room temperature and collected. The humins were completely soluble [HS3] in the reaction mass and non-sticky [S0] to the equipment. Then the organic phase was separated from aqueous phase and subjected to pH adjustment to about 7 by NaHCO$_3$. Further said organic phase was subjected to first distillation to recover furfural as low boiling product. The remaining organic phase contained isophorone with dissolved humins; equipment contained no humins at all. This method achieved 100% conversion of xylose present in the feedstock with 69% yield of furfural.

Example 7 [See Table Serial No 10]

3.5 kg of a concentrated stream [first stream] comprising 10% xylose by weight was obtained from an acid pre-treated biomass like corncob, corn stover or sugarcane bagasse. This stream also comprised 1.5% to 2% sulphuric acid by weight and 0.5% to 1.0% oxalic acid by weight used in said pre-treatment reaction. Then said first stream was subjected to pH adjustment to a pH value of 1.6 using a 50% NaOH solution forming a second stream. Then a mixture of 2800 g methyl isobutyl ketone (MIBK) and 700 g isophorone (80:20) was added to said second stream forming a third stream. This third stream was then subjected to temperature of 180° C. in a stirred tank reactor working at 650 RPM for 1 hour. After the completion of heat treatment the reaction mass was cooled to room temperature, filtered to remove precipitated humins and then subjected to phase separation. The humins were partially soluble [HS2] in the reaction mass and non-sticky [S0] to the equipment. The organic phase was washed with alkali to neutralise acids and was subjected to distillation to recover MIBK that was recycled in the process. The remaining organic phase containing furfural and isophorone was subjected to a second distillation to recover furfural in pure form. The undistilled bottom fraction remaining after the separation of MIBK and furfural from organic mass contained mainly isophorone (ISP) with soluble humins along with small quantity of hydroxymethyl furfural (HMF). This ISP-humins mixture was recycled to the process without affecting the process performance in terms of conversion of xylose and the yield of furfural. To this end, some quantity of this ISP-humins mixture is taken out (purged) from said bottom faction and the remaining mass used in the process along with fresh make-up ISP and MIBK. This operation is continued until the soluble humins in ISP was concentrated to a level of 60% by weight. At this time, the whole ISP-humins mixture was removed and distilled to recover pure ISP solvent. This method achieved 98% conversion of xylose present in the feedstock with 80% yield of furfural.

Example 8

TABLE 1 lists different experiments of preparation of furfural from xylose under different reaction conditions and parameters including the example described herein above. All common parameters were kept at standard conditions of temperature at 180° C., reaction time at 1 hour, pH at 1.6, and RPM at 650, except the variable parameters under study as depicted in the table. The efficiencies of conversion of xylose and yield of furfural afforded by using the methods of the invention disclosed herein are listed to show the general utility of the invention and its features. It was observed that the significant amounts of humins were formed when MIBK or toluene was used as a solvent. It was also found that the humins formed in reaction were sticking to the internal part of the rectors; and this further led to the problem of processing such reaction mass for recovery of furfural and said solvent. Further, the process could not be run continuously as the reactor chambers were choked with insoluble and sticky humins. On the other hand when isophorone alone or in combination with other solvents was used, the most of the humins were dissolved in the isophorone without affecting the efficiencies of process. Further said isophorone with humins and other components could be recycled at least five times in the process significantly increasing the economics of the furfural production. The solubility of humins in reaction mass on completion of reaction at room temperature was qualitatively defined as HS0=insoluble, HS1=sparingly soluble, HS2=partially soluble and HS3=completely soluble. Similarly, the stickiness of humins to internal parts of the reactor at room temperature was qualitatively defined as S0=non-sticking, S1=nominally sticking, S3=partially sticking and S3=significantly sticking.

Example 9

A concentrated stream comprising 20% xylose by weight was obtained from an acid pre-treated biomass like corncob, corn stover or sugarcane bagasse as above. This stream was subjected to pH adjustment to a pH value of 1.6 using a 50% NaOH solution. Then 2000 g of mixture of methyl isobutyl ketone and isophorone, made in the proportion of 80:20, was charged to a 10-L closed stirred tank reactor with 2000 g of 20% xylose stream; and subjected to temperature of 180° C. and RPM of 650 for 1 hour at time of start up step. After 1 hour, the xylose stream and the mixed solvents steam each was pumped to the reactor simultaneously maintaining the temperature at about 180° C. The rate of addition for each of xylose and mixed solvents was 60 mL/min. The reaction mass was continuously discharged using a backpressure regulator at a rate of 120 mL/min. This continuous process was run for 3 hours forming 21 kg of reacted mass. This hot mass was passed through a heat exchanger to cool it to room temperature. Then the mass was filtered to remove precipitated humins and subjected to phase separation. This method achieved 78% conversion of xylose with 75% selectivity of furfural production.

Example 10

A concentrated stream comprising about 20% xylose by weight was obtained from an acid pre-treated biomass like corncob, corn stover or sugarcane bagasse as above. This stream was subjected to pH adjustment to a pH value of 1.6 using a 50% NaOH solution. This 20% xylose stream and a mixture of methyl isobutyl ketone and isophorone [made in the proportion of 80:20] was charged separately to feed tanks. Initially, the mixture of solvents at a flow rate of 10 ml/min was passed through a pre-heater set at about 160° C. and then introduced to a 4-L packed column [plug flow] reactor. Then the above pH adjusted 20% xylose stream was introduced at a flow rate of 10 ml/min maintaining the temperature of reactor about 180° C. The whole reaction system was maintained at 18 bars under nitrogen pressure. The reaction mass was discharged to a receiver [pressure vessel] held at room temperature through a heat exchanger. The pressure in the system including receiver was maintained at 18 bar using a backpressure regulator. This continuous process was run for 6 hours forming 7.2 kg of reacted mass. Then the mass was filtered to remove precipitating humins and subjected to phase separation. This method achieved 85% conversion of xylose with 75% selectivity of furfural production.

While the invention has been particularly shown and described with reference to embodiments listed in examples, it will be appreciated that several of the above disclosed and other features and functions, or alternatives thereof, may be desirably combined into many other different systems or applications. Also that various presently unforeseen and unanticipated alternatives, modifications, variations, or improvements therein may be subsequently made by those skilled in the art which are also intended to be encompassed by the following claims. Although the invention has been described with reference to specific preferred embodiments, it is not intended to be limited thereto, rather those having ordinary skill in the art will recognise that variations and modifications may be made therein which are within the spirit of the invention and within the scope of the claims.

These and further experimental data are summarized in TABLE 1. Further experiments can be processed according to the above disclosure and teaching.

TABLE 1

PREPARATION OF FURFURAL IN DIFFERENT CONDITIONS FROM THE C5 STREAM.

| No. | SOLVENT MIXTURE | SOLVENT MIXTURE RATIO | XYLOSE in C5 STREAM [%] | AQUEOUS: ORGANIC PHASE RATIO | WET HUMINS [g] | SELEC-TIVITY [%] | CONVER-SION [%] | YIELD [%] | HUMINS SOLUBILITY * | STICK-INESS ** |
|---|---|---|---|---|---|---|---|---|---|---|
| 1 | MIBK ONLY | X | 10 | 1:1 | 65 | 80 | 99 | 79 | HS2 | S1 |
| 2 | MIBK ONLY | X | 10 | 1:3.2 | 5 | 78 | 100 | 78 | HS2 | S1 |
| 3 | MIBK ONLY | X | 20 | 1:1 | 250 | 70 | 100 | 70 | HS2 | S1 |
| 4 | MIBK ONLY | X | 20 | 1:3.2 | 85 | 81 | 98 | 79 | HS2 | S1 |
| 5 | ISP ONLY | X | 10 | 1:1 | 0 | 83 | 97 | 81 | HS3 | S0 |
| 6 | ISP ONLY | X | 10 | 1:3.2 | 0 | 76 | 99 | 75 | HS3 | S0 |
| 7 | ISP ONLY | X | 20 | 1:1 | 40 | 69 | 100 | 69 | HS3 | S0 |
| 8 | ISP ONLY | X | 20 | 1:0.75 | 45 | 73 | 100 | 73 | HS3 | S0 |
| 9 | ISP ONLY | X | 20 | 1:3.2 | 35 | 75 | 99 | 74 | HS3 | S0 |
| 10 | MIBK:ISP | 80:20 | 10 | 1:1 | 50 | 82 | 98 | 80 | HS2 | S0 |
| 11 | MIBK:ISP | 80:20 | 15 | 1:1 | 159 | 77 | 99 | 76 | HS2 | S1 |
| 12 | MIBK:ISP | 80:20 | 20 | 1:1 | 195 | 78 | 100 | 78 | HS2 | S1 |
| 13 | MIBK:ISP | 80:20 | 20 | 1:3.2 | 70 | 73 | 100 | 73 | HS2 | S1 |

TABLE 1-continued

PREPARATION OF FURFURAL IN DIFFERENT CONDITIONS FROM THE C5 STREAM.

| No. | SOLVENT MIXTURE | SOLVENT MIXTURE RATIO | XYLOSE in C5 STREAM [%] | AQUEOUS: ORGANIC PHASE RATIO | WET HUMINS [g] | SELEC- TIVITY [%] | CONVER- SION [%] | YIELD [%] | HUMINS SOLUBILITY * | STICK- INESS ** |
|---|---|---|---|---|---|---|---|---|---|---|
| 14 | MIBK:ISP | 80:20 | 20 | 1:0.75 | 300 | 69 | 100 | 69 | HS2 | S1 |
| 15 | MIBK:ISP | 80:20 | 20 | 1:0.5 | 400 | 59 | 100 | 59 | HS2 | S1 |
| 16 | TOLUENE ONLY | X | 20 | 1:1 | 221 | 82 | 99 | 81 | HS0 | S3 |
| 17 | TOLUENE:ISP | 80:20 | 10 | 1:1 | 145 | 86 | 98 | 84 | HS1 | S3 |
| 18 | TOLUENE:ISP | 80:20 | 20 | 1:3.2 | 84 | 74 | 99 | 73 | HS1 | S3 |
| 19 | TOLUENE:ISP | 80:20 | 20 | 1:1 | 410 | 69 | 100 | 69 | HS1 | S3 |
| 20 | TOLUENE:ISP | 60:40 | 20 | 1:3.2 | 128 | 76 | 99 | 75 | HS1 | S3 |
| 21 | TOLUENE:ISP | 50:50 | 20 | 1:3.2 | 175 | 68 | 100 | 68 | HS2 | S2 |
| 22 | TOLUENE:ISP | 40:60 | 20 | 1:3.2 | 56 | 70 | 99 | 69 | HS2 | S2 |
| 23 | CYCLO- HEXANONE ONLY | X | 20 | 1:1 | 50 | 8 | 100 | 8 | HS3 | S0 |
| 24 | MIBK:ISP | 80:20 | 25 | 1:1 | 345 | 56 | 99 | 55 | HS0 | S3 |

ISP = Isophorone,
MIBK = Methyl Isobutyl Ketone
* Humins solubility in organic phase at room temperature: HS0: insoluble, HS1: sparingly soluble, HS2: partially soluble, HS3: completely soluble
** Stickiness to reactor internal parts at room temperature: S0: non-sticking, S1: nominally sticking, S2: partially sticking, S3: significantly sticking

We claim:

1. A process for converting xylose to furfural comprising:
   (a) providing a first stream comprising xylose obtained from an acid pre-treated lignocellulosic biomass, the first stream having a pH;
   (b) adjusting the pH of said first stream with a first base forming a second stream, the first base comprising a metal oxide or hydroxide;
   (c) mixing said second stream with isophorone or a mixture of at least one first solvent and at least one second solvent forming a third stream;
   (d) treating said third stream in a reactor for a specific time period so as to cause a desired reaction forming a fourth stream;
   (e) separating said fourth stream into an organic stream and an aqueous stream, said organic stream having a pH;
   (f) adjusting the pH of said organic stream with a second base;
   (g) separating furfural as the product from a fraction comprising or consisting of humins and the at least one second solvent or isophoron; and
   (h) recycling or recovering the at least one second solvent or isophorone.

2. The process of claim 1, wherein said first stream comprises xylose between 10% to 30% by weight.

3. The process of claim 1, wherein the pH of said organic stream is adjusted to 7.

4. The process of claim 1, wherein the metal oxide or hydroxide used to adjust the pH of said first stream is selected from the group consisting of sodium hydroxide and magnesium oxide.

5. The process of claim 1, wherein the second base used to adjust the pH of said organic stream is selected from the group consisting of sodium hydroxide, monoethanolamine and sodium bicarbonate.

6. The process of claim 1, further comprising recycling said at least one first solvent and said at least one second solvent separated from said organic stream.

7. The process of claim 1, wherein said second solvent solubilises at least a portion of the humins formed in said process.

8. The process of claim 1, wherein conversion efficiency of xylose is more than 90% by weight.

9. The process of claim 1, wherein the yield of furfural is at least 60% by weight of xylose.

10. The process of claim 1, wherein said reactor is selected from the group consisting of a batch reactor, a continuous stirred-tank reactor and a continuous plug-flow reactor.

11. A process for the preparation of furfural from lignocellulosic biomass, the process comprising:
   (a) acid pre-treating the lignocellulosic biomass forming a first stream comprising xylose, said first stream having a pH;
   (b) adjusting the pH of said first stream with a first base forming a second stream, the first base comprising a metal oxide or hydroxide;
   (c) mixing said second stream with isophorone forming a third stream;
   (d) treating said third stream in a reactor for a specific time period so as to cause a reaction forming a fourth stream;
   (e) separating said fourth stream into an organic stream and an aqueous stream, said organic stream having a pH;
   (f) adjusting the pH of said organic stream with a second base;
   (g) separating furfural as the product from a fraction comprising or consisting of humins and the isophoron; and
   (h) recycling or recovering the at least one solvent or isophorone.

12. The process of claim 1, wherein said reactor is selected from the group consisting of a continuous stirred-tank reactor and a continuous plug-flow reactor.

13. The process of claim 1, further comprising at least of separating, recycling, or recovering the at least one first solvent separated from said organic stream.

14. The process of claim 1, wherein said first stream is obtained from the acid pre-treated lignocellulosic material after removal of insoluble fraction.

15. The process of claim 1, wherein said first solvent is methyl isobutyl ketone or toluene.

16. The process of claim 1, wherein said second solvent is isophorone.

17. The process of claim 1, wherein treating said third stream in a reactor for a specific time period comprises treating said third stream in a reactor at a temperature for a specific time period, wherein said temperature ranges from about 160° C. to about 220° C.

18. The process of claim 1, wherein said specific time period ranges from 10 minutes to 120 minutes.

19. The process of claim 1, wherein said pH of said first stream is adjusted to between 1 and 2.

20. The process of claim 11, further comprising removing an insoluble fraction from the acid pre-treated lignocellulosic to form the first stream.

* * * * *